United States Patent [19]

Lane

[11] Patent Number: 4,501,030
[45] Date of Patent: Feb. 26, 1985

[54] METHOD OF LEAFLET ATTACHMENT FOR PROSTHETIC HEART VALVES

[75] Inventor: Ernest Lane, Huntington Beach, Calif.

[73] Assignee: American Hospital Supply Corporation, Evanston, Ill.

[21] Appl. No.: 293,667

[22] Filed: Aug. 17, 1981

[51] Int. Cl.³ .............................................. A61F 1/00
[52] U.S. Cl. ................................................ 3/1.5; 3/1
[58] Field of Search .................... 3/1.5, 1; 128/334 R, 128/334 C; 137/525.1, 525

[56] References Cited

U.S. PATENT DOCUMENTS

4,106,129  8/1978  Carpentier et al. ...................... 3/1.5
4,192,020  3/1980  Davis et al. ................................ 3/1.5

Primary Examiner—Richard J. Apley
Assistant Examiner—David J. Isabella
Attorney, Agent, or Firm—Gordon L. Peterson

[57] ABSTRACT

A prosthetic heart valve including a frame having a plurality of commissure supports, a plurality of resilient supports, and a plurality of valve leaflets. The valve leaflets are attached to the resilient supports, and the resilient supports lie radially outwardly of the commissure supports, respectively. When in use, the valve is subjected to forces which are used to clamp the valve leaflets between the resilient supports and the commissure supports to augment whatever other leaflet attachment techniques may be used.

30 Claims, 18 Drawing Figures

METHOD OF LEAFLET ATTACHMENT FOR PROSTHETIC HEART VALVES

BACKGROUND OF THE INVENTION

Prosthetic heart valves are used to replace diseased natural heart valves in the aortic, mitral, tricuspid and pulmonary positions in the heart. Examples of three such valves are shown in Carpentier et al U.S. Pat. No. 4,106,129, Ionescu et al U.S. Pat. No. 4,084,268 and Davis et al U.S. Pat. No. 4,192,020. As shown by these patents, a prosthetic heart valve typically includes a frame formed of a wire or a shell and valve leaflets attached to the frame.

One of the major problems with prosthetic leaflet heart valves, including bioprosthetic valves, is insufficient long-term durability resulting from failure of the valve leaflets in the area of their attachment to the frame. Many different attachment techniques have been attempted, including stitching, gluing, integral and dip molding, clamping and combinations of these methods.

Stitching was the earliest method used to attach the valve leaflets in a prosthetic heart valve; however, disruption of the leaflet material at the suture lines produced a number of failures Gluing has not proved reliable and it is generally used in conjunction with other methods, such as clamping or stitching. Integral molding has also proven to be not reliable, and dip molding is not preferred because it can only be used with certain materials, such as polyurethane. An additional disadvantage of integral molding is that it cannot be used with biological materials because of the high temperatures involved in the molding process.

One reason for failure of the valve leaflets is that, during diastole in the aortic position and systole in the mitral position, a radial inward tensile force is applied to the valve leaflets. This tensile force imposes loads on whatever leaflet attachment means is utilized and can ultimately be destructive. For example, when stitching is utilized, the tensile force imposes high shear stress which can ultimately result in valve leaflet failure.

SUMMARY OF THE INVENTION

This invention provides a clamping action on the valve leaflet to augment whatever other leaflet attachment means is used. The clamping action of this invention enables various other leaflet attachment means, such as sutures, to be used and increases the life of the valve.

Because the clamping action is not the sole means for leaflet retention, the clamping forces are less than would be required if the clamping action were the sole leaflet attachment means. Thus, this invention provides a reduced clamping force, and consequently, the leaflets do not take a permanent set, whereas the leaflets would tend to take a permanent set if they were permanently clamped with sufficient force to attach the leaflets.

In addition, the clamping force varies with forces applied to the valve when the valve is in use, and preferably, there is essentially no clamping force on the leaflets before implantation. This further reduces the likelihood of damage to the leaflets or of the leaflets taking a permanent set in response to the clamping force.

To provide the clamping action, this invention utilizes the tensile force which tends to cause failure of the valve leaflet attachment means. This tensile force reduces during valve opening, and this contributes to the variable nature of the clamping force. The clamping force can be applied over a large area of the valve leaflet to further reduce the likelihood of damage to the leaflet.

This concept can be advantageously implemented in a prosthetic heart valve which comprises a generally annular frame having a plurality of commissure supports, a resilient valve leaflet support attached to the frame adjacent a first frame section, and valve leaflet sheet material mounted on the frame to define a plurality of valve leaflets which are movable between open and closed positions. The first of the valve leaflets is drivingly coupled to the resilient support so that a radial inward force on the first valve leaflet deflects the resilient support radially inwardly. A region of the first valve leaflet extends between the resilient support and the first frame section. The resilient support and the first frame section are located so that the resilient support can deflect and press the region of the first valve leaflet against the first frame section in response to a force which deflects the support radially inwardly. Thus, the resilient support and the frame cooperate to define a clamp which is operated by the tensile force which occurs during valve closure.

In a typical construction, the valve leaflet sheet material includes a section of valve leaflet sheet material for each of the valve leaflets, and the valve leaflets are attached to each other. In a preferred construction, the frame has two circumferentially spaced frame sections defining an opening through which the valve leaflets extend, and each of the frame sections cooperates with the resilient support to clamp one of the valve leaflets during diastole. For example, the valve leaflets can be attached by sutures, and the clamping substantially reduces the shearing stresses in the valve leaflets at the sutures.

Another advantage of this construction is that, when the valve leaflets open abruptly, e.g., systolic ejection through the aortic valve, the leaflet material can separate uniformly and closely simulate the ideal central flow orifice of a natural valve and distribute the stresses uniformly along the free edges of the valve leaflets. This is in contrast to valves which utilize a tuck stitch to hold the valve leaflets together radially inwardly of the frame at the commissures. The tuck stitch, which is eliminated by this invention, induces intensified stresses in the valve leaflet as the valve leaflets fully open. It has been postulated that these stresses can lead to early failure of the leaflet material, Broom, Neil D. "Fatigue-Induced Damage In Gluteraldahyde-Preserved Heart Valve Tissue,", *Journal of Thoracic And Cardiovascular Surgery*, 76 #2 August 1978.

This invention also provides a resilient wire frame which maximizes the opening of the prosthetic heart valve and which has no sharp bends or kinks of the type which would reduce the valve opening or be incompatible with the tissue with which it will be in contact during use. The frame of this invention is constructed of wire formed into an annular configuration and having a plurality of circumferentially spaced apical sections joined by curved sections, with each of the apical sections including a reverse bend. The apical sections extend in the same direction. To allow attachment to the valve leaflets with a minimum of discontinuities and to reduce the overall axial dimension of the valve without sharp bends in the wire, each of the curved sections is substantially elliptical as viewed in side elevation and forms a portion of an ellipse.

The frame can advantageously be constructed by a method which includes forming a wire into a generally flat pattern, with the wire having a plurality of part-substantially elliptical sections joined by apical sections and with each of the apical sections including a reverse bend. The apical sections extend in the same general direction, and the wire has opposite ends. The flat pattern is then formed into an annular configuration, and the opposite ends of the wire are joined to retain the wire in the annular configuration.

The means for joining the opposite ends of the wire inherently provide a discontinuity in the frame. To minimize the effect of this discontinuity, the wire terminates in straight, tangent sections of one of the apical sections, and the tangent sections are tangent to the associated reverse bend and the associated elliptical section, respectively. The joining means can advantageously take the form of a splice which joins such tangent sections.

The valve of this invention has other advantageous features. For example, the valve can be constructed in two separate sub-assemblies, and then the two sub-assemblies are attached. Thus, a fabric cover is attached to the wire frame to form one sub-assembly, and the valve leaflet sheet material is attached to valve leaflet supports to form a second sub-assembly. The second sub-assembly is then inserted up into recesses formed by the first sub-assembly and attached in place.

The invention, together with further features and advantages thereof, may best be understood by reference to the following description taken in connection with the accompanying illustrative drawing.

DESCRIPTION OF THE PREFERRED EMBODIMENT

Figure 1:
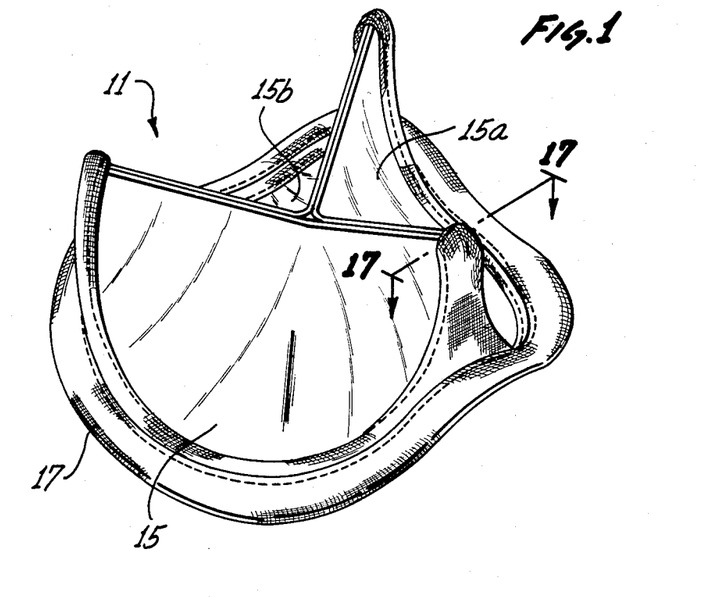
FIG. 1 is a perspective view of a bioprosthetic heart valve constructed in accordance with the teachings of this invention.

FIG. 1 shows a prosthetic heart valve 11 which generally comprises a frame 13 (FIG. 2), three identical valve leaflets 15, 15a and 15b, and a suture ring 17. In the embodiment illustrated, the suture ring 17 is scalloped, and accordingly, the heart valve is an aortic heart valve; however, this is merely illustrative inasmuch as the features of this invention are equally applicable to other heart valves which would employ suture rings of other configurations. Similarly, the valve leaflets 15, 15a and 15b may be tissue or be a synthetic material, such as film polytetrafluoroethylene.

The frame 13 is preferably constructed of a wire; however, certain features of this invention, such as the intermittent clamping feature, do not require that the frame be constructed of wire. The frame may be constructed of various biocompatible materials, such as suitable metals, plastics or composite fibrous materials. For example, a suitable cobalt alloy, a polyolefin or a carbon reinforced, non-metallic material may be used.

Figure 3:
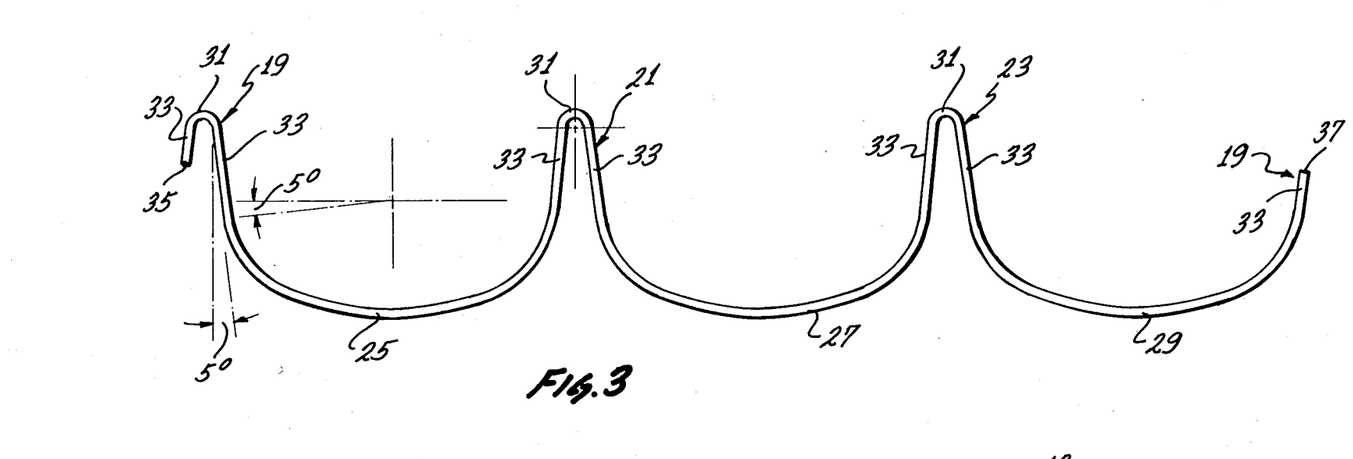
FIG. 3 is a side elevational view of the wire formed into a flat pattern in the first step of making the wire frame.

According to a preferred method of making the frame 13, the wire is formed into a flat pattern as shown in FIG. 3. The wire has commissure supports 19, 21 and 23 integrally joined by curved sections 25, 27 and 29. Each of the commissure supports is identical and extends in the same direction. Each of the commissure supports 19, 21 and 23 may be considered as forming, or including, an apical section, each of which includes a reverse bend 31 and two frame sections or segments which form tangents 33 joining the opposite ends of the associated reverse bend to the adjacent curved sections. The wire terminates at opposite ends 35 and 37 at one of the tangents 33 of the commissure support 19. Each of the tangents 33 is linear, and the tangents 33 of each of the commissure supports diverge as they extend away from the associated reverse bend 31.

Each of the curved sections 25, 27 and 29 is identical and preferably forms a part of an ellipse. For example, in the embodiment illustrated, each of the curved sections extends for 170 degrees, and each of the reverse bends 31 is circular and also extends for 170 degrees. The included angle formed by an extension of the axes of the tangents 33 of each of the commissure supports may be, for example, ten degrees. This specific dimensional data is given by way of illustration only, and the concepts of this invention relating to the frame do not require these particular dimensions.

The flat pattern shown in FIG. 3 contains no kinks or sharp bends, and the tangents 33 blend smoothly into the adjacent reverse bends and curved sections. Similarly, the curved sections 25, 27 and 29 and the reverse bends 31 provide no kinks or sharp corners.

Figure 8:
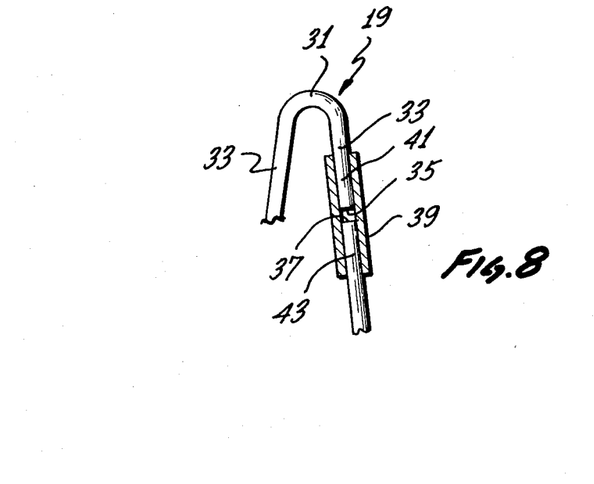
FIG. 8 is a fragmentary view partially in section showing one form of splice for attaching the opposite ends of the wire together.

Next, the flat pattern of FIG. 3 is formed into an annular, cylindrical configuration, and the opposite ends 35 and 37 are joined together in any suitable manner, such as by splicing, using a sleeve 39 which is a cylindrical sleeve. Splicing together the opposite ends of a wire frame for a heart valve is shown in Carpentier et al U.S. Pat. No. 4,106,129. However, the frame of the present invention differs from the frame of the Carpentier et al patent in that the wire terminates in the ends 35 and 37 at the straight tangent 33 of the commissure support 19. Accordingly, the presence of the straight cylindrical sleeve 39 on the correspondingly straight tangent 33 for splicing the ends 35 and 37 does not alter the configuration of the wire or cause the wire to kink or form a sharp end. By way of contrast, if the wire terminated in the ends 35 and 37 in one of the curved sections 25, 27 and 29, or one of the reverse bends 31, the sleeve 39 would have to be carefully correspondingly curved, and crimping of the curved sleeve to avoid kinks would be difficult. If a straight sleeve were used, it would cause kinks in the wire, which is undesirable. With this invention, the tangent 33 on which the sleeve 39 is carried, may be considered as including tangent sections 41 and 43 which are spliced together by the sleeve 39.

Figure 2:
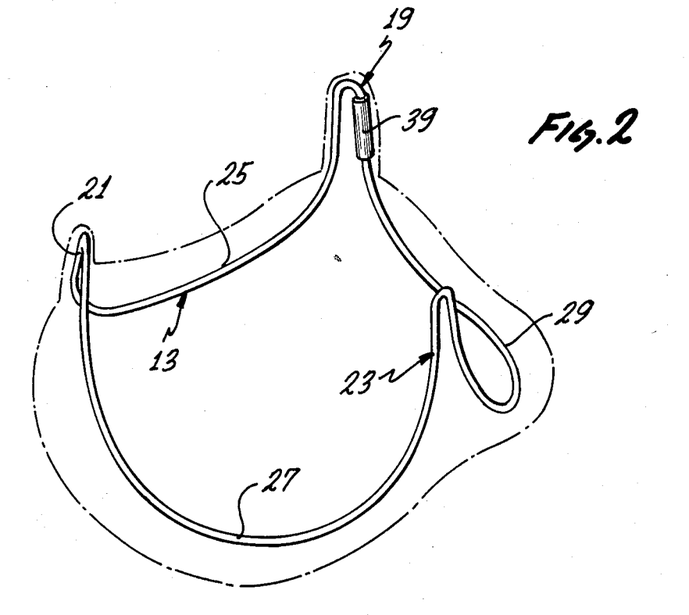
FIG. 2 is a perspective view of a preferred form of wire frame, with the outline of the valve being shown in phantom lines.
Figures 7, 9, 11, 12, 13:
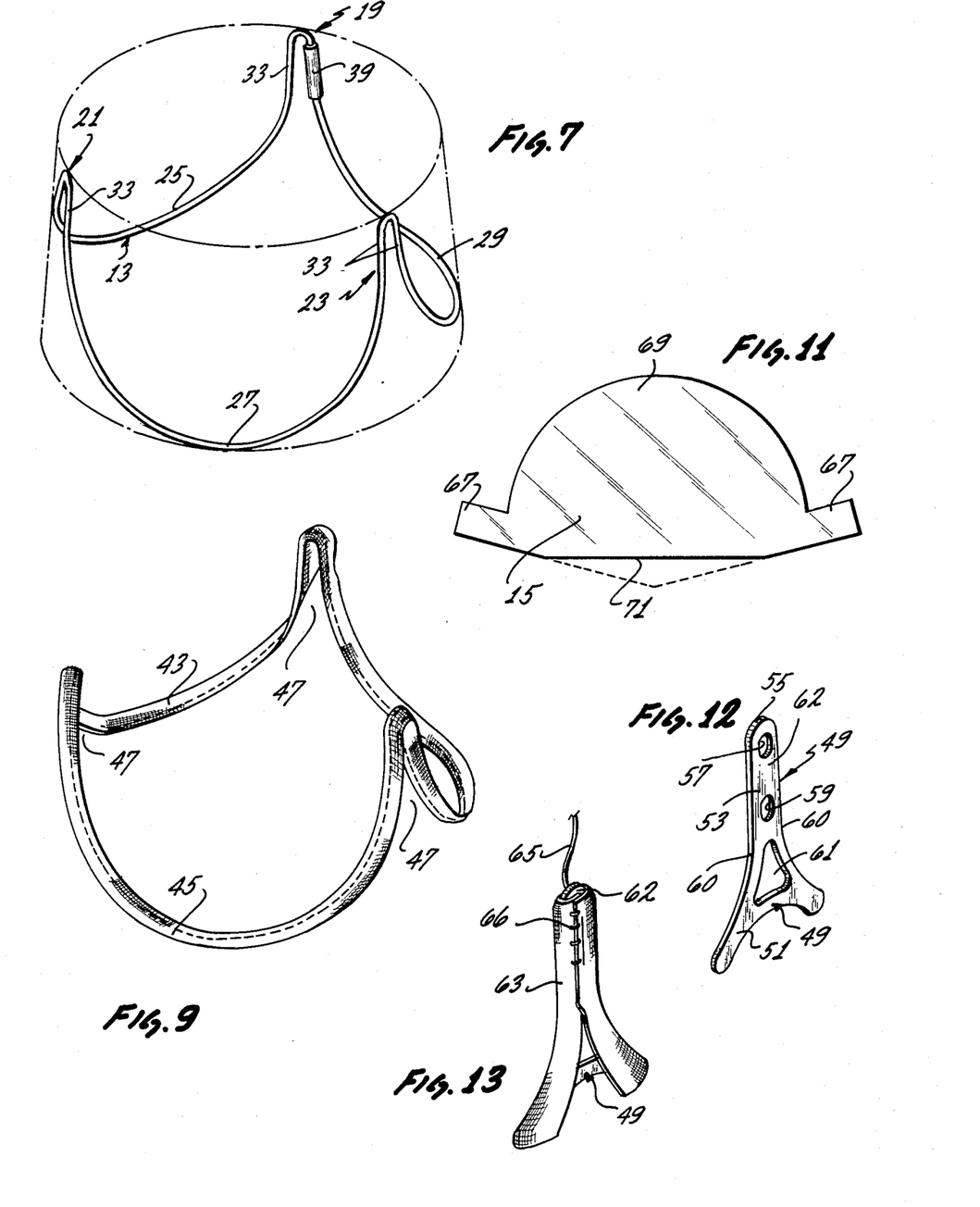
FIG. 7 is a perspective view showing the completed wire frame formed into an annular, frusto-conical configuration.
FIG. 9 is a perspective view similar to FIG. 7 showing a subassembly which comprises the wire frame and a fabric cover.
FIG. 11 is a plan view of one form of valve leaflet.
FIG. 12 is a perspective view of one form of resilient support.
FIG. 13 is a perspective view of the resilient support and a fabric skirt attached to the support.

According to the preferred method, the final step in constructing the frame 13 is to form the cylindrical annular configuration into a frusto-conical annular configuration as shown in FIGS. 2 and 7. In this configuration, the commissure supports 19, 21 and 23 are inclined toward each other as they extend away from their associated curved sections 25, 27 and 29. By way of example, the configuration of the frame 13 in FIG. 2 is a frustum of a right circular cone with each of the commissure supports 19 being inclined radially inwardly at about five degrees. Although the wire is formed from the flat configuration of FIG. 3 to the frusto-conical configuration of FIG. 2 (or FIG. 7), the curved sections 25, 27 and 29 remain in an elliptical configuration as viewed in side elevation, the tangents 33 remain straight and the reverse bends 31 remain part circular. However, the aspect ratio of the partial ellipses formed by the curved sections 25, 27 and 29 is altered somewhat. The frame 13, including the commissure supports 19, 21 and 23, is resiliently flexible and can better accommodate shock loading.

Figure 4:
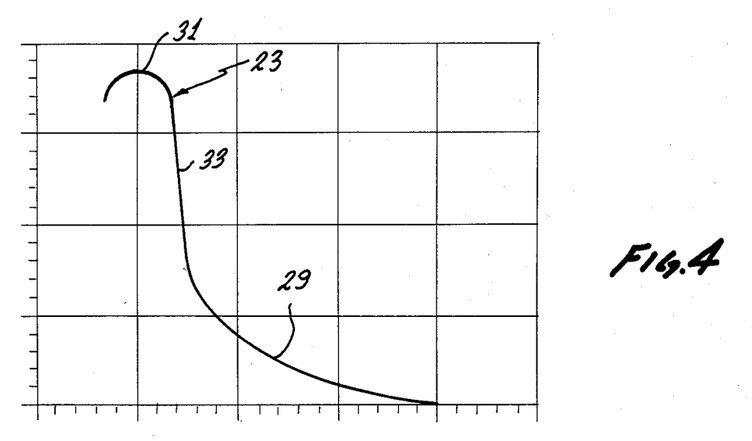
FIGS. 4-6 are line diagrams showing the centerline configuration of the wire frame in front elevation, side elevation and top plan, respectively.
Figure 5:
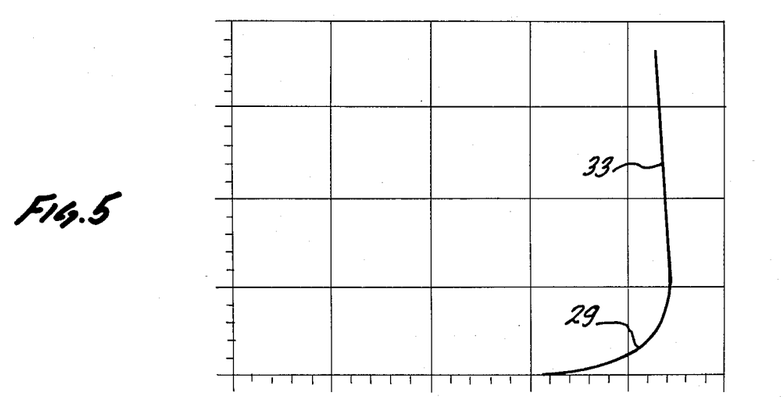
Figure 6:
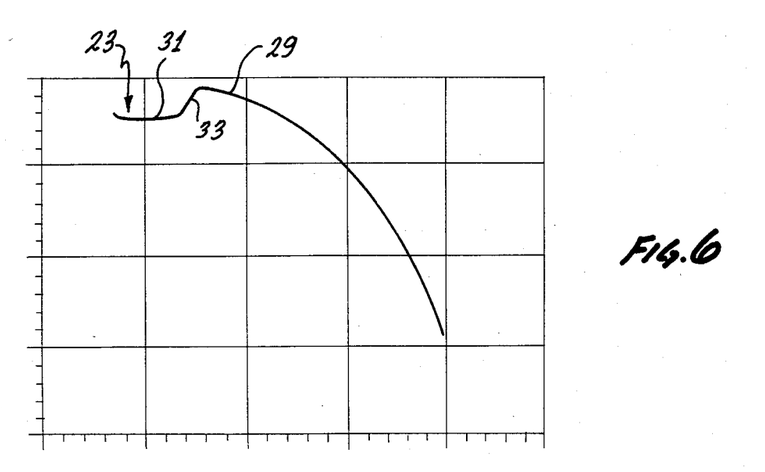

FIGS. 4-6 illustrate how the wire frame 13 provides a smoothly curved contour at all locations along the frame, and in particular, along and adjacent the commissure support 23, it being understood that the commissure supports 19 and 21 are identical to the commissure support 23. FIGS. 4-6 show the center line of the wire in line diagram form, and it can be seen that smooth curves exist in all three views. FIG. 4, which is a side elevational view, illustrates one half of the part elliptical configuration of the curved section 29.

Figure 10:
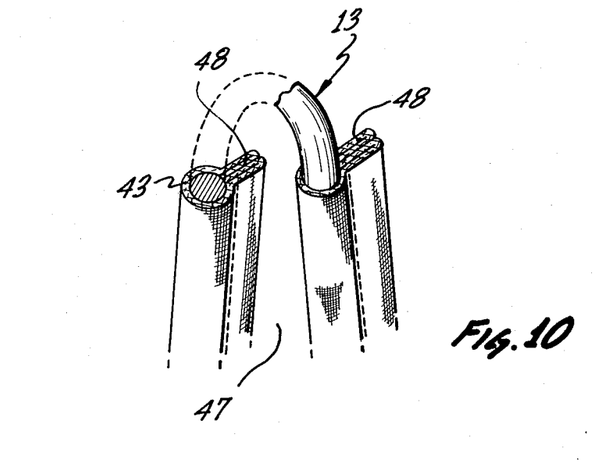
FIG. 10 is a fragmentary perspective view with the fabric cover in section illustrating the fabric cover and frame at one of the commissure supports.

Next, the frame 13 is covered with a fabric cover 43, and the cover is attached to the frame in any suitable manner, such as by sutures 45. This forms a subassembly which has three recesses 47 which open away from the associated reverse bend, i.e., downwardly as viewed in FIG. 9. As shown in FIG. 10, the cover 43 completely encloses the wire frame 13 and has a pair of flaps 48 which extend radially outwardly of the frame.

Figures 14, 15:
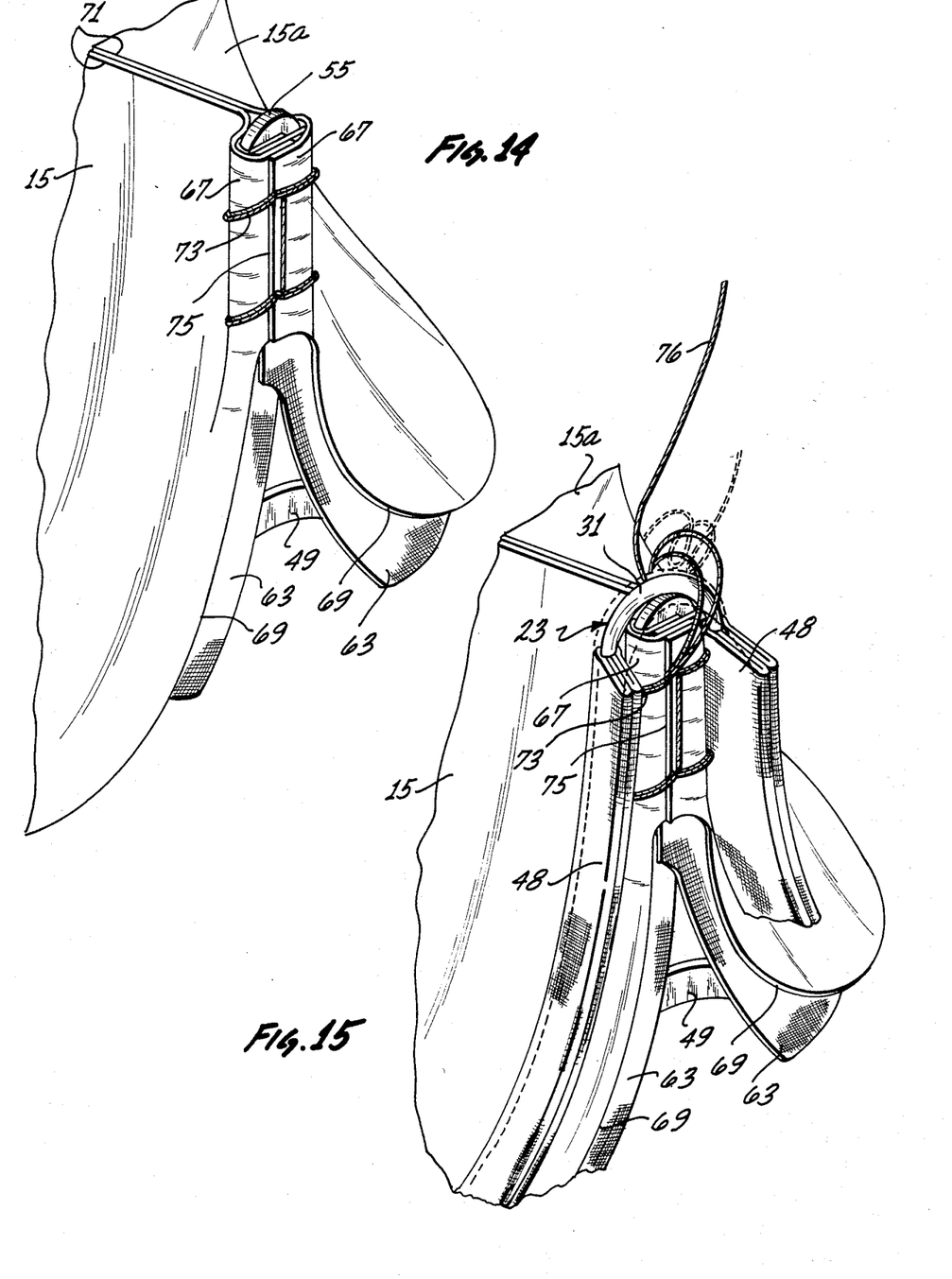
FIG. 14 is a fragmentary perspective view of the resilient support-valve leaflet subassembly.
FIG. 15 is a fragmentary perspective view of the two subassemblies being stitched together, with portions of the fabric cover being broken away.

The preferred method also includes forming a second subassembly as shown in FIG. 14 and attaching the two subassemblies as shown in FIG. 15. This latter subassembly includes a plurality of identical, resilient, valve leaflet supports 49 (FIG. 12). One of the resilient supports 49 is provided for each of the commissure supports 19, 21 and 23, and accordingly, in the embodiment illustrated, there are three of the resilient supports 49. The resilient support 49 may be of various different constructions provided that it is resilient and that the valve leaflets 15-15b can be attached thereto. In the embodiment illustrated, the resilient support 49 is constructed of a suitable plastic material, such as Mylar, and it is elongated. The resilient support 49 is of integral construction and has a relatively wide base 51, an elongated shank 53 with a curved upper end 55 and suture holes 57, 59 and 61. As shown in FIG. 12, the resilient support 49 is in the form of a relatively flat sheet, with side edges 60 and a radial outer face 62.

Each of the resilient supports 49 is then covered with a fabric skirt 63, and the fabric skirt is attached to the support in any suitable manner, such as by a suture 65 which extends through the skirt 63 and one or more of the suture holes 57, 59 and 61 to define a seam 66 on the outer face 62.

The valve leaflets 15, 15a and 15b are formed of suitable valve leaflet sheet material. In the embodiment illustrated, each of the valve leaflets 15, 15a and 15b is made up from an individual section of the valve sheet leaflet sheet material. FIG. 11 shows one form that the valve leaflet 15 might assume when laid out flat, it being understood that the other valve leaflets may be identical. In the form shown in FIG. 11, the valve leaflet 15 has attaching tabs 67, an elliptical edge 69 extending between the tabs 67 and an edge 71 forming a shallow trough and extending from a lower (as viewed in FIG. 11), central region outwardly to the tabs 67. The dashed line in FIG. 11 shows the original configuration of the edge 71 before cutting.

To complete the subassembly shown in FIG. 14, the valve leaflets 15, 15a and 15b are attached to the resilient supports 49. As shown in FIG. 14, the valve leaflets 15 and 15a are attached to one of the resilient supports 49. In the embodiment illustrated, this is accomplished by wrapping one of the tabs 67 of each of these two leaflets part-way around the resilient support 49 and then attaching these tabs to the support 49 in any suitable manner, such as by sewing utilizing a suture 73. The suture 73 extends through the tab 67, the skirt 63 and the suture holes 57 and 59. This forms a seam 75 which extends along the seam 66 on the outer face 62 of the resilient support 49 to attach the leaflet to the support 49 of the leaflet mounting means.

When mounted in this fashion, the edges 71 extend radially inwardly from a location adjacent the upper end 55 of the support 49 to define commissures. The elliptical edges 69 are draped over the side edges 60 of the support 49 and overlie portions of the outer face 62 of the support 49.

The construction shown in FIG. 14 is typical for the other two supports 49. Thus, the other tab 67 of the valve leaflet 15 is attached to a tab 67 of the valve leaflet 15b at a second of the supports 49, and the other tabs 67 of the valve leaflets 15a and 15b are attached to the third resilient support 49.

Figure 16:
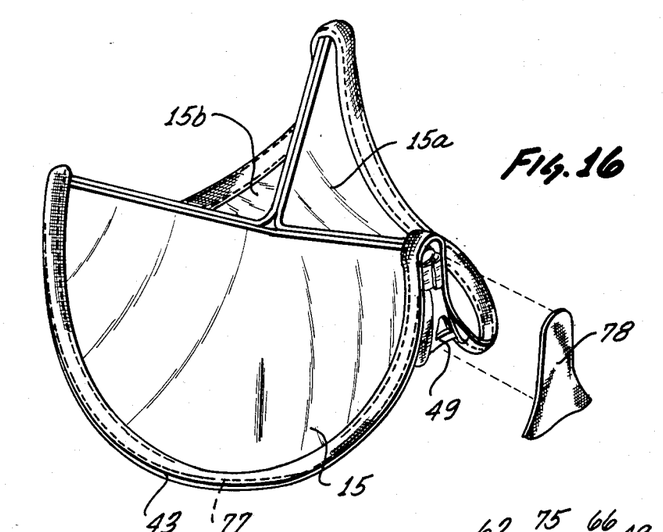
FIG. 16 is a perspective view illustrating the two subassemblies fully attached to each other.

The next step in the construction of the heart valve 11 is the insertion of the subassembly of FIG. 14 into the recesses 47 of the subassembly of FIG. 9 as shown in FIGS. 15 and 16. Specifically, the supports 49 are inserted into the recesses 47, respectively, to a location closely adjacent the reverse bends 31, with the supports lying radially outwardly of the associated commissure supports. The valve leaflets 15 and 15a extend from the support 49 to which they are attached radially inwardly through the recess 47 and into the interior of the frame 13.

With the two subassemblies in the position shown in FIG. 15, they are attached to each other, and this is preferably carried out in two stages. In the first stage, the supports 49 are attached to the associated commissure supports 19, 21 and 23 in any suitable manner, such as by a suture 76 which is passed through the tab 67 of the valve leaflets 15, 15a, the skirt 63, the suture holes 57 and 59, and passed over the reverse bend 31. This is done several times, and the suture is then suitably tied off. This initial attachment step holds the two subassemblies together in the proper orientation so that a marginal portion of the valve leaflets 15, 15a and 15b lying along the elliptical edges 69 can be attached to the cover 43 as by sewing utilizing a suture 77 as shown in FIG. 16. To enable the heart valve to be implanted in a heart, the suture ring 17 is then attached to the frame 13 in any suitable manner, such as by sewing it to the cover 43, the flaps 48 are sewed closed, and woven cloth 78 (FIG. 16) is sewed to the outside faces of the flaps to form the configuration of FIG. 1.

Figures 17, 18:
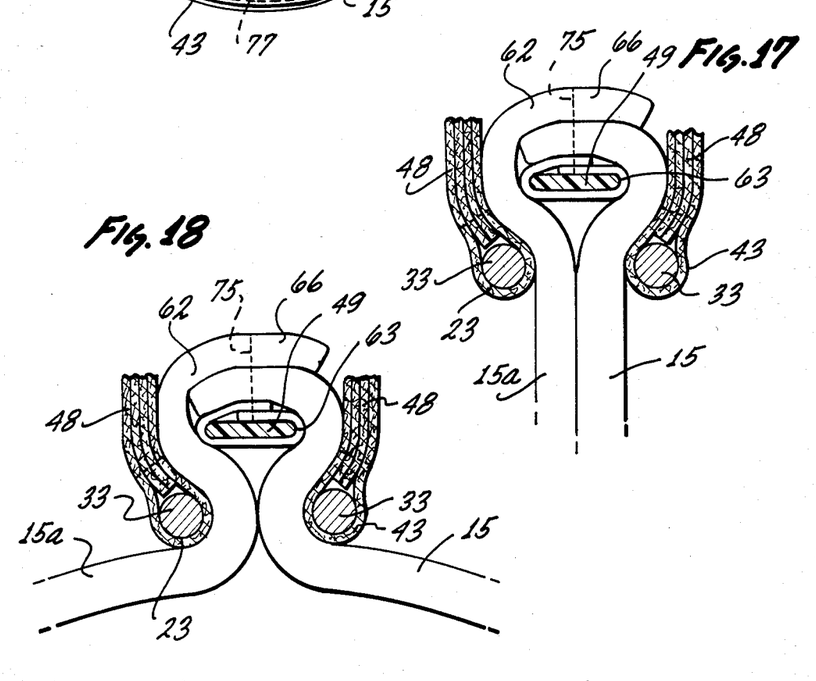
FIG. 17 is a fragmentary sectional view taken generally along line 17—17 of FIG. 1, with the valve leaflets closed.
FIG. 18 is a fragmentary sectional view taken along line 17—17 of FIG. 1 with the valve leaflets open.

FIGS. 17 and 18 further show the structural orientation of the support 49 and the segments or tangents 33 of the frame and how they cooperate to provide a clamping force on the valve leaflets. The tangents 33 and the surrounding portions of the cover 43 are spaced circumferentially to define an opening which is a portion of the recess 47. The support 49 is located radially outwardly of the opening and the tangents. The seams 66 and 75 lie radially outwardly of the support 49 along the outer face 62. Regions of the leaflets 15 and 15a extend from the support 49 along a path which extends between the support and the segments 33 and through the opening to the interior of the frame. FIGS. 17 and 18 are taken at the juncture of the tangents 33 and the associated bend 31, and in that plane, the spacing between the covers 43, as measured along a line between the centers of the tangents, equals twice the thickness of the leaflets 15 and 15a.

When the valve closes, a tensile force F acts radially inwardly on the valve leaflets 15 and 15a. The resilience of the support 49 is selected so that the tensile force can resiliently deform the support 49 radially inwardly to clamp regions of the valve leaflets 15 and 15a between the support 49 and the tangents 33. More particularly, these regions are clamped between the relatively soft fabric cover 43 on the frame 13, and the relatively soft fabric skirt 63 on the support 49. This clamping action of the members 33 and 49 of the valve leaflet mounting means protects the seam 75. In other words, some of the reaction force required to offset the tensile force F is provided by the clamping action to thereby reduce the stresses in the valve leaflets 15 and 15a along the seam 75. The resilience of the support 49 also prevents shock loading of the valve leaflets 15 and 15a. The commissure support 23 resiliently deforms radially inwardly so it does not form a hard stop which could provide shock loading, and the fabric cover 43 and the fabric skirt 63 form a cushion.

During operation of the valve 11, the forces on the valve leaflets, the segments 33 and the support 49 vary, and thus, the clamping force on the leaflets also varies as the clamping force is a function of whatever forces act on the segments 33 and the support 49 to move them to clamp or unclamp the leaflet. For example, when the leaflets 15 and 15a open as shown in FIG. 18, the tensile force F reduces, and the resilient support 49 resiliently moves toward its normal position in which there is sufficient space between it and the tangents 33 to reduce the clamping force and, if desired, by appropriately selecting the resilience of the supports 49 and the commissure supports, the clamping force can be periodically reduced to zero. Thus, the clamping force provided is variable and can be made intermittent if desired. In opening, the leaflets 15 and 15a separate uniformly and closely simulate the ideal central flow orifice of a natural valve and distribute the stresses uniformly along the free edges of the valve leaflets.

Although an exemplary embodiment of the invention has been shown and described, many changes, modifications and substitutions may be made by one having ordinary skill in the art without necessarily departing from the spirit and scope of this invention.

I claim:

1. A prosthetic heart valve subject to a force when in use comprising:
    means defining a plurality of valve leaflets;
    means for mounting said valve leaflets for opening and closing movement and in a configuration suitable for a prosthetic heart valve; and
    said mounting means including first means for attaching at least one of the valve leaflets to said mounting means and second means including first and second members responsive to the force on the valve when the valve is in use for clamping a region of said one valve leaflet between said first and second members to augment the attachment provided by said first means and reduce the stress on said first means.

2. A valve as defined in claim 1 wherein at least one of said first and second members is resilient.

3. A valve as defined in claim 1 wherein said mounting means includes a frame which includes first and second frame sections and an opening between said frame sections, said first member includes siad first frame section and said second member includes a resilient support adjacent said opening, said one valve leaflet is on said resilient support and extends through said opening and between said resilient support and said first frame section whereby said region of said one valve leaflet can be clamped between said resilient support and said first frame section.

4. A prosthetic heart valve subject to a force when in use comprising:
    means for defining a plurality of valve leaflets;
    means for mounting said valve leaflets for opening and closing movement in a configuration suitable for a prosthetic heart valve; and
    said mounting means including first means responsive to the force on the prosthetic heart valve when the valve is in use for clamping at least one of said valve leaflets with a clamping force to assist in retaining said one valve leaflet on the mounting means, said first means including first and second resilient members for clamping said one valve leaflet.

5. A valve as defined in claim 4 wherein said first means is responsive to the force on said one valve leaflet for increasing said clamping force said one valve leaflet and is responsive to said force diminishing for reducing the clamping force on said one valve leaflet.

6. A prosthetic heart valve comprising:
    a generally annular frame having a plurality of commissure supports, at least one of said commissure supports including a first frame section;
    a resilient support;
    means for attaching said resilient support to said frame with said support being adjacent said first frame section;

valve leaflet sheet material mounted on said frame to define a plurality of valve leaflets which are movable between open and closed positions, a first of said valve leaflets being drivingly coupled to the resilient support so that a radial inward force on said first valve leaflet deflects said resilient support radially inwardly;

a region of the first valve leaflet extending between the resilient support and the first frame section; and said resilient support and said first frame section being located so that, the resilient support can deflect and press said region of the first valve leaflet against said first frame section in response to a force which deflects the resilient support radially inwardly.

7. A valve as defined in claim 6 including suture means for attaching the first valve leaflet to said resilient support.

8. A valve as defined in claim 6 wherein said frame is resilient whereby the first frame section can deflect when said region of the first valve leaflet is pressed against it by the support.

9. A valve as defined in claim 6 wherein said frame includes a second frame section circumferentially spaced from said first frame section to define an opening, said attaching means attaches the resilient support to the frame with said support being adjacent said opening, a second of said valve leaflets is drivingly coupled to the resilient support so that a radial inward force on the second valve leaflet deflects said resilient support radially inwardly, a region of the second valve leaflet extends between the resilient support and the second frame section, means for attaching said first and second valve leaflets together at a location intermediate said regions and adjacent said support, said first and second valve leaflets extend through said opening, and said resilient support and said second frame section being located so that the resilient support can deflect and press said region of the second valve leaflet against said second frame section in response to a force which deflects the resilient support radially inwardly.

10. A valve as defined in claim 6 wherein the commissure supports are resilient and covered with fabric, said resilient support being covered with fabric.

11. A valve as defined in claim 9 wherein the attachment of the first and second valve leaflets forms a composite valve leaflet, said resilient support has a surface facing radially outwardly, said composite valve leaflet extends along said resilient surface of said resilient support and said attaching means for said first and second valve leaflets includes suture means.

12. A valve as defined in claim 6 wherein said frame includes a wire formed into an annular configuration and defining a plurality of circumferentially spaced apical sections joined by curved sections, each of said commissure supports includes one of said apical sections, each of said curved sections is substantially elliptical in side elevation and forms a portion of an ellipse.

13. A valve as defined in claim 6 wherein said frame includes a wire formed into an annular configuration and having a plurality of circumferentially spaced apical sections joined by curved sections, each of said commissure supports includes one of said apical sections, each of said apical sections includes a reverse bend and first and second tangents joining the opposite ends of such reverse bend of such apical sections to the adjacent curved sections, respectively, said wire having ends at one of said tangents, and said valve including means for joining said ends together at said one tangent.

14. A method of making a frame for a prosthetic heart valve comprising:

forming a wire into a generally flat pattern with the wire having a plurality of part substantially elliptical sections joined by apical sections and with each of the apical sections including a reverse bend, said apical sections extending in the same general direction and said wire having opposite ends, said substantailly elliptical sections being substantially elliptical in a direction perpendicular to the flat pattern;

forming the flat pattern into an annular configuration; and joining said opposite ends to retain the wire in said annular configuration whereby the overall axial dimension of the frame is reduced without introducing sharp bends into the wire.

15. A method as defined in claim 14 wherein a first of said apical sections has a straight segment which is tangent to the associated reverse bend and the associated elliptical section, said wire terminates in said segment, and said step of joining includes joining said ends at said segment.

16. A method as defined in claim 14 wherein each of said apical sections has first and second straight segments joining the opposite ends of the reverse bend of such apical section to the adjacent elliptical sections, respectively, when the wire is in said annular configuration and said step of joining includes splicing said opposite ends of said wire at one of said segments.

17. A method as defined in claim 16 wherein said step of forming the flat pattern includes forming the wire into a frustum of a cone whereby said apical sections extend toward each other as they extend away from the associated elliptical sections, said step of forming the wire forms said segments of each of the apical sections so that the segments of each such apical section extend away from each other as they extend from the associated reverse bend toward the associated elliptical sections, and there are three of said apical sections.

18. A frame for a prosthetic heart valve comprising:

a wire formed into an annular configuration and having a plurality of circumferentially spaced apical sections joined by curved sections, each of the apical sections including a reverse bend, said apical sections extending in the same direction; and each of said curved sections being substantially elliptical as viewed from the side of the annular configuration and forming only a portion of an ellipse whereby the overall axial dimension of the frame is reduced without introducing sharp bends into the wire.

19. A frame as defined in claim 18 wherein a first of said apical sections has a tangent which is tangent to the associated reverse bend and the associated curved section, said wire has opposite ends at said segment, and said frame includes means for joining said opposite ends at said segments.

20. A frame as defined in claim 18 wherein said apical sections are resilient and are inclined inwardly as they extend away from the elliptical sections.

21. A frame for a prosthetic heart valve comprising:

a wire formed into an annular configuration and having a plurality of circumferentially spaced apical sections joined by curved sections, each of said apical sections including a reverse bend and first and second straight segments joining the opposite ends of the reverse bend of such apical section to the adjacent curved sections, respectively;

said wire having opposite ends at one of said segments; and means for splicing said opposite ends of said wire together at said one of said segments.

22. A prosthetic heart valve comprising:

a frame of generally annular configuration having a plurality of commissure supports, each of said commissure supports extending in the same general direction;

each of said commissure supports including segments spaced circumferentially to define an opening;

a plurality of valve leaflet supports for the commissure supports, respectively;

means for attaching the valve leaflet supports to the frame with each of the valve leaflet supports being positioned generally radially outwardly of the associated commissure supports;

valve leaflet sheet material; and means for attaching the valve leaflet sheet material to the valve leaflet supports and to the frame to define a plurality of valve leaflets which are movable between open and closed positions with said valve leaflet sheet material extending from each of the supports to which it is joined through the opening of the associated commissure support.

23. A valve as defined in claim 22 including a fabric cover on said frame, each of said commissure supports and the associated fabric cover forming a recess opening in a direction which is opposite to the direction in which the commissure supports extend, and said valve leaflet supports being received within said recesses, respectively.

24. A valve as defined in claim 22 wherein said valve leaflet sheet material includes a plurality of sections of sheet material defining said valve leaflets, respectively, means for attaching adjacent valve leaflets together adjacent the valve leaflet supports, respectively, each of said valve leaflet supports having a surface facing radially outwardly, and said valve leaflet sheet material including portions lying radially outwardly of each of said valve leaflet supports.

25. A valve as defined in claim 24 wherein each of said valve leaflet supports is resilient and can deflect toward the associated commissure support to press regions of the valve leaflets against the commissure supports.

26. A valve as defined in claim 25 wherein the frame includes wire having part elliptical curved sections joining the commissure supports, at least one of the commissure supports has a reverse bend and a segment joining the reverse bend to the adjacent curved section, said wire having opposite ends at said segment and means for splicing said opposite ends of said wire together at said segment.

27. A method of making a prosthetic heart valve comprising:

providing a first subassembly including an annular wire frame having a cloth cover with the frame having a plurality of circumferentially spaced commissure supports joined by curved sections and with each of the commissure supports including a reverse bend and circumferentially spaced wire segments joining such reverse bend to the adjacent curved sections, respectively, to form a recess at each commissure support which opens away from the associated reverse bend;

attaching valve leaflet sheet material to a plurality of valve leaflet supports with the number of the valve leaflet supports corresponding to the number of the commissure supports to form a second subassembly;

inserting the second subassembly into said recesses to a location adjacent said reverse bends with the valve leaflet supports lying radially outwardly of the associated commissure supports and with the valve leaflet sheet material extending from the associated valve leaflet supports radially outwardly through the adjacent recesses; and attaching the subassemblies.

28. A method as defined in claim 27 wherein there are three of said commissure supports, three of said valve leaflet supports, and said valve leaflet sheet material includes three sections of valve leaflet sheet material and including attaching adjacent sections of the valve leaflet sheet material to each other adjacent each of said supports prior to said step of inserting.

29. A method as defined in claim 27 including attaching a suturing ring to said cover.

30. A valve as defined in claim 6 wherein said resilient support lies radially outwardly of the first frame section and said first valve leaflet has a portion which is wrapped at least part way around the resilient support and lies radially outwardly of the resilient support.

* * * * *

UNITED STATES PATENT OFFICE
CERTIFICATE OF CORRECTION

Patent No. 4,501,030   Dated Feb. 26, 1985

Inventor(s) Ernest Lane

It is certified that error appears in the above-identified patent and that said Letters Patent are hereby corrected as shown below:

Column 1, line 25 after "failures" insert a period.

Column 4, line 15 after "heart valve" insert -- 11 --.

Column 8, line 34 change "siad" to -- said --.

Column 8, line 58 after "force" insert -- on --.

Column 9, line 11 after "so that" delete the comma.

Column 10, line 56 replace "tangent" with -- straight segment --

Signed and Sealed this

Thirtieth Day of July 1985

[SEAL]

Attest:

DONALD J. QUIGG

Attesting Officer   Acting Commissioner of Patents and Trademarks